US008834780B2

(12) United States Patent
Ying et al.

(10) Patent No.: US 8,834,780 B2
(45) Date of Patent: Sep. 16, 2014

(54) HYDRODYNAMIC SPINNING OF POLYMER FIBER IN COAXIAL LAMINAR FLOWS

(75) Inventors: Jackie Y. Ying, Singapore (SG); Min Hu, Singapore (SG); Rensheng Deng, Singapore (SG); Karl Schumacher, Singapore (SG); Motoichi Kurisawa, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 99 days.

(21) Appl. No.: 12/920,066

(22) PCT Filed: Mar. 2, 2009

(86) PCT No.: PCT/SG2009/000078
§ 371 (c)(1),
(2), (4) Date: Aug. 27, 2010

(87) PCT Pub. No.: WO2009/108138
PCT Pub. Date: Sep. 3, 2009

(65) Prior Publication Data
US 2011/0006453 A1  Jan. 13, 2011

Related U.S. Application Data

(60) Provisional application No. 61/064,369, filed on Feb. 29, 2008.

(51) Int. Cl.
| | |
|---|---|
| *B29C 63/06* | (2006.01) |
| *D01D 5/24* | (2006.01) |
| *A61L 27/52* | (2006.01) |
| *D01D 5/38* | (2006.01) |
| *D01D 5/28* | (2006.01) |

(52) U.S. Cl.
CPC .. *D01D 5/28* (2013.01); *D01D 5/24* (2013.01); *A61L 27/52* (2013.01); *D01D 5/38* (2013.01)
USPC ................. 264/563; 264/172.15; 264/173.11; 264/172.11; 264/172.16; 264/171.27

(58) Field of Classification Search
None
See application file for complete search history.

(56) References Cited

U.S. PATENT DOCUMENTS

| | | | |
|---|---|---|---|
| 4,276,172 A | 6/1981 | Henne et al. | |
| 5,480,598 A * | 1/1996 | Gentile et al. | 264/41 |

(Continued)

FOREIGN PATENT DOCUMENTS

| | | |
|---|---|---|
| JP | 01-221506 | 9/1989 |
| JP | H06-508547 | 9/1994 |

(Continued)

OTHER PUBLICATIONS

International Search Report and Written Opinion, mailed Apr. 14, 2009, in related PCT patent application No. PCT/SG2009/000078.

(Continued)

*Primary Examiner* — Monica Huson
(74) *Attorney, Agent, or Firm* — Klarquist Sparkman, LLP (57) ABSTRACT

A polymer fiber is formed by hydrodynamic spinning. Fluids are forced to flow through a conduit to form a laminar flow comprising three or more layers of generally coaxial fluid flows, at respective flow rates selected to define a cross-section of a tubular middle layer of the fluid flows. The middle layer comprises a cross-linkable polymer precursor. Another layer of the fluid flows comprise a cross-linking agent. The polymer precursor, cross-linking agent and fluids are selected to prevent substantial diffusion of the polymer precursor away from the middle layer, and to allow a portion of the cross-linking agent to diffuse from the another layer into the middle layer to facilitate cross-linking of the polymer precursor in the middle layer to form a tubular polymer layer in a polymer fiber. The polymer layer thus has a cross-section generally corresponding to the cross-section of the middle layer.

25 Claims, 10 Drawing Sheets

(56) References Cited

U.S. PATENT DOCUMENTS

| | | | |
|---|---|---|---|
| 5,770,193 | A | 6/1998 | Vacanti et al. |
| 6,347,930 | B1 | 2/2002 | Muscat et al. |
| 7,033,603 | B2 | 4/2006 | Nelson et al. |
| 2007/0037138 | A1* | 2/2007 | Winther .............................. 435/5 |

FOREIGN PATENT DOCUMENTS

| | | |
|---|---|---|
| JP | H09-038473 | 2/1997 |
| WO | 93/12868 | 7/1993 |
| WO | 01/66835 A1 | 9/2001 |
| WO | 2005/035726 A2 | 4/2005 |
| WO | 2006/019293 A1 | 2/2006 |
| WO | 2007/007051 A1 | 1/2007 |

OTHER PUBLICATIONS

International Preliminary Report on Patentability, mailed Apr. 14, 2009, in related PCT patent application No. PCT/SG2009/000078.
Albrecht et al., "Preparation of Highly Asymmetric Hollow Fiber Membranes from Poly(ether Imide) by a Modified Dry-Wet Phase Inversion Technique Using a Triple Spinneret," Journal of Membrane Science, 2005, vol. 262, pp. 69-80.
Boontheekul et al., "Controlling Alginate Gel Degradation Utilizing Partial Oxidation and Bimodal Molecular Weight Distribution," Biomaterials, 2005, vol. 26, pp. 2455-2465.
Crow et al., "Release of Bovine Serum Albumin from a Hydrogel-Cored Biodegradable Polymer Fiber," Biopolymers, 2006, vol. 81 pp. 419-427.
Kenis et al., "Microfabrication Inside Capillaries Using Multiphase Laminar Flow Patterning," Science, 1999, vol. 285, pp. 83-85.
Kim et al., "Microfluidic 3-Dimensional Encapsulation System by Self-Assembling Peptide Hydrogel," Journal of the Association for Laboratory Automation, 2006, vol. 11, pp. 352-359.
Knight et al., "Hydrodynamic Focusing on a Silicon Chip: Mixing Nanoliters in Microseconds," Physical Review Letters, 1998, vol. 80, No. 17, pp. 3863-3866.
Kurisawa et al., "Injectable Biodegradable Hydrogels Composed of Hyaluronic Acid-Tyramine Conjugates for Drug Delivery and Tissue Engineering," Chemical Communications, 2005, vol. 34, pp. 4312-4314.
Leob et al., "Sea Water Demineralization by Means of an Osmotic Membrane," Advances in Chemistry Series, 1962, vol. 38, pp. 117-132.
European Patent Office, Extended European Search Report mailed Mar. 16, 2011 in related EP Application No. 09715162.5.
Shin et al., "'On the Fly' Continuous Generation of Alginate Fibers Using a Microfluidic Device", Langmuir, 2007, vol. 23, pp. 9104-9108.
Takei et al., "Development of mammalian cell-enclosing calcium-alginate hydrogel fibers in a co-flowing stream," Bilotechnology Journal, 2006, vol. 1, pp. 1014-1017.
Chinese Patent Office, "Office Action", Oct. 25, 2011, in related Chinese Patent Application No. 200980115470.X.
Notice of Reasons for Rejection dated Aug. 5, 2013, issued in corresponding Japanese Patent Application No. 2010-548647, 7 pages.

* cited by examiner

HYDRODYNAMIC SPINNING OF POLYMER FIBER IN COAXIAL LAMINAR FLOWS

CROSS-REFERENCE TO RELATED APPLICATION

This application claims the benefit of U.S. provisional application No. 61/064,369, filed Feb. 29, 2008, the entire contents of which are incorporated herein by reference.

FIELD OF THE INVENTION

The present invention relates generally to preparing polymer fibers, and particularly to forming polymer fibers in multiphase laminar flows.

BACKGROUND OF THE INVENTION

Polymer fibers such as hydrogel fibers are useful as carriers or scaffolds in various applications, for example, for cell transplantation or tissue engineering. It is desirable to seed cells in the fibers in some applications, such as in the fields of vascular and kidney tissue engineering. However, it remains a challenge to efficiently form polymer fibers with variable cross-sectional shapes and sizes, or to control the cell seeding in the fibers. Polymer fibers with seeded cells may be formed using an extrusion process but it is inconvenient to vary the fiber cross-sectional shape or size in a conventional extrusion process, or to control how cells are dispersed in the fiber.

SUMMARY OF THE INVENTION

A convenient process of fiber formation utilizes a laminar flow of three or more layers of fluid flows to shape and polymerize middle or inner layer(s) to form polymer fiber layer(s). The cross-section (including shape and size) of the fiber layer can be conveniently adjusted by changing the input flow rates of the respective layers of fluid flows. Cells may be conveniently and selectively incorporated into the fiber by including the cells in the precursor fluid.

Therefore, in accordance with an aspect of the present invention, there is provided a process of forming a polymer fiber by hydrodynamic spinning, comprising forcing a plurality of fluids to flow through a conduit and to form a laminar flow comprising three or more layers of generally coaxial fluid flows. The fluid flows flow at respective flow rates through the conduit selected to define a cross-section of a tubular middle layer of the fluid flows. The middle layer comprises a cross-linkable polymer precursor. Another layer of the fluid flows comprises a cross-linking agent. The polymer precursor, cross-linking agent, and fluids are selected to prevent substantial diffusion of the polymer precursor away from the middle layer, and to allow a portion of the cross-linking agent to diffuse from the another layer into the middle layer to facilitate cross-linking of the polymer precursor in the middle layer to form a tubular polymer layer in a polymer fiber. The polymer layer thus has a cross-section generally corresponding to the cross-section of the middle layer.

The flow rates through the conduit may be adjusted to change the cross-section of the tubular middle layer, such as when the fluid flows are forced through the conduit. The flow rates may be adjusted by adjusting a ratio of the flow rates. The other layer may comprise a tubular outer layer of the fluid flows. The other layer may comprise an inner layer of the fluid flows, and the polymer fiber may be tubular. The tubular polymer fiber may have an inner diameter of about 20 µm or larger, and an outer diameter of about 60 µm or larger. A generally cylindrical inner layer of the fluid flows may comprise the polymer precursor, and the polymer fiber may be generally cylindrical. The cylindrical polymer fiber may have a diameter of about 20 µm or larger. The middle layer may comprise a plurality of middle layers, and the polymer fiber may comprise a plurality of polymer layers. The cross-linking agent may comprises a cross-linker, and the polymer layer may comprise a polymer formed by cross-linking the polymer precursor with the cross-linker. The cross-linking agent may comprise a cross-linking initiator. The cross-linking agent may comprise a cross-linking catalyst. The polymer fiber may be solidified. The polymer fiber may be immersed in a liquid bath after the polymer fiber has exited the conduit. A cell may be dispersed in the laminar flow so that the polymer fiber comprises the cell. Cells may be dispersed in a plurality of the layers of the laminar flow so that a plurality of layers in the polymer fiber comprise cells. The cells may be dispersed in the laminar flow such that different layers of the polymer fiber comprise different types of cells, or that different layers of the polymer fiber comprise different concentrations of cells. One or more of the fluids may comprises a cell culture medium. One or more of the fluids comprises phosphate buffered saline. The polymer precursor may comprise gelatin-hydroxyphenylpropionic acid, calcium alginate, or polysulfone. The cross-linking agent may comprise hydrogen peroxide. The middle layer of the fluid flows may comprise horseradish peroxidase. The process may comprise initiating cross-linking in the middle layer.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION OF EXEMPLARY EMBODIMENTS

An exemplary embodiment of the present invention relates to a process for forming a polymer fiber by hydrodynamic spinning. A plurality of fluids are forced to flow through a conduit and to form a laminar flow comprising three or more layers of generally parallel fluid flows. The layers of fluid flows are generally coaxial. The respective flow rates of the fluid flows in the conduit are selected, such as by adjusting the input fluid flow rates, to define the cross-section of a tubular middle layer of the fluid flows, particularly the cross-sectional size. The flow rates may be pre-adjusted, or dynamically adjusted by adjusting the input flow rates while the polymer fiber is being formed. The middle layer contains a polymer precursor. One or more other layers of the fluid flows contain a cross-linking agent, which may be a cross-linker, a cross-linking initiator, or a cross-linking catalyst. The polymer precursor, cross-linking agent and the fluids are selected to prevent substantial diffusion of the polymer precursor away from the middle layer, but allow a portion of the cross-linking agent to diffuse from the other layer(s) into the middle layer. Crosslinking of the polymer precursor can then occur in the middle layer in the presence of the crosslinking agent, to form a tubular polymer layer. The polymer layer has a cross-section generally corresponding to the cross-section of the middle layer of the fluid flows. The polymer layer may form a polymer fiber, or a layer in a multi-layer fiber in the laminar flow. Cells may be conveniently incorporated into a fiber layer by selectively dispersing the cells in the fluid flows.

As will be further described below, with three or more layers of fluid flows in the laminar flow, solid or hollow fibers may be conveniently formed from this process. A hollow fiber may have an inner diameter of less than about 20 µm and an outer diameter of larger than about 60 µm. A solid fiber may have a diameter of larger than about 20 µm.

With three or more layers of fluid flows in the laminar flow, a fiber with multiple layers may also be conveniently formed. Conveniently, the different fiber layers may have different physical, chemical or biological properties.

Figure 1:
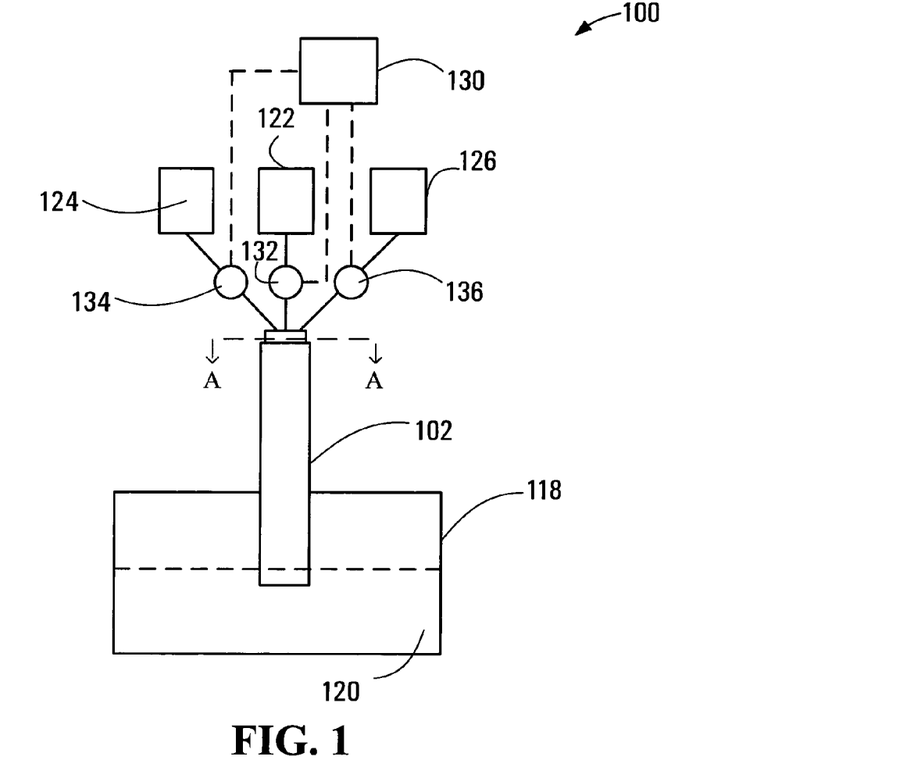
FIG. 1 is a schematic diagram illustrating a spinning apparatus 100 with a spinneret, exemplary of an embodiment of the present invention.
Figure 2:
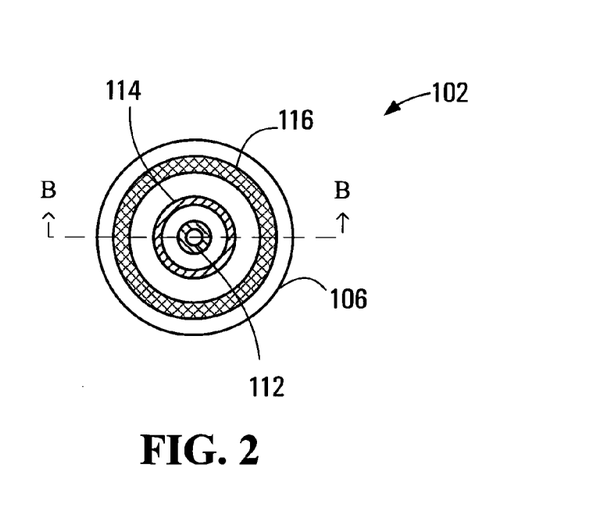
FIG. 2 is a cross-sectional view of the spinneret shown in FIG. 1 along the line A-A.
Figure 3:
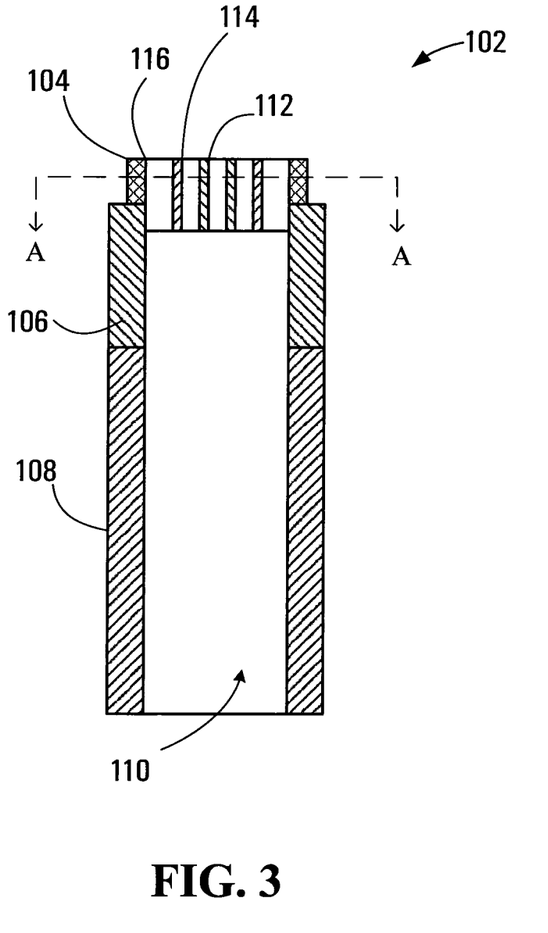
FIG. 3 is a cross-sectional view of the spinneret of FIG. 2 along the line B-B.

An exemplary spinning extrusion apparatus 100 is schematically illustrated in FIGS. 1, 2 and 3.

Apparatus 100 includes a spinneret 102, which has an inlet section 104, a connecting section 106, and a polymerizing section 108 defining a conduit 110.

Inlet section 104 includes three generally coaxially nested tubular inlets 112, 114, 116, each in fluid communication with a fluid source (see below) for injecting a respective fluid into conduit 110.

Connecting section 106 directs the fluids from inlets 112, 114, 116 into conduit 110, to form a laminar flow in conduit 110. Connecting section 106 may have a generally cylindrical shape, as shown in FIG. 3, or a generally funnel shape (see below).

Polymerizing section 108 is sufficiently long to allow polymerization of the polymer precursor by cross-linking.

Conduit 110 may have a generally circular cross-section with a diameter of, e.g., about 0.8 mm, and a length of, e.g., about 15 mm. The diameter and length may be varied depending on the particular application. However, as can be understood, the dimensions and shape of conduit 110 should be such that it allows laminar fluid flows therein for the particular fluids and flow rate ranges to be used in the particular application. For example, the diameter of conduit 110 should be such that for the given fluids and fluid flow rates, the Reynolds number (Re) of the fluid flow in conduit 110 will be smaller than the threshold value for forming laminar flow.

Inlet section 104, connecting section 106 and polymerization section 108 may be provided separately, or integrated into a unitary body.

A container 118 containing a liquid bath 120 may be placed adjacent conduit 110 for immersing a polymer fiber spun from conduit 110 in liquid bath 120. The liquid bath 120 may include a fluid for solidifying the fiber or reducing tension on the fiber surface. For example, the bath may include a phosphate buffered saline (PBS) solution.

Two or more fluid sources, such as fluid sources 122, 124, 126, may be provided.

One of the fluid sources, such as fluid source 124, supplies a first (precursor) fluid containing a polymer precursor. The polymer precursor may include macromolecules that have a low tendency to diffuse through an interface between different fluid layers in a laminar flow. The polymer precursor may also be cross-linkable by a cross-linker to form a polymer. More than one polymer precursors may be included. Different monomers that can be copolymerized may also be included. For example, the polymer precursor may include gelatin-hydroxyphenylpropionic acid (Gtn-HPA), calcium alginate, or polysulfone. Other precursors such as fibrinogen, hyaluronic-acid, gelatin-tyramine, chitin, N-isopropylacrylamide, or the like may also be used in different applications. When a list of items is provided with an "or" before the last item herein, any one of the items may be included or used; and a combination of any two or more of the items may also be included or used, as long as the combination is possible and the combined items are not inherently incompatible or exclusive.

Another fluid source, such as fluid source 122 or 126, supplies a cross-linking agent fluid containing a cross-linking agent. The cross-linking agent may be a cross-linker, a crosslinking initiator, or a cross-linking catalyst. A cross-linker may be selected to cross-link the polymer precursor to form a polymer fiber when the polymer precursor and the cross-linker are injected into conduit 110 and brought into contact. Alternatively, a cross-linking initiator may be selected to initiate cross-linking of the polymer precursor when the cross-linking initiator is present in the precursor fluid. A catalyst may be used to catalyze the cross-linking and polymerization reactions so that the reactions can proceed at sufficient rates to form polymers before the flows exit conduit 110 and loose their cross-sectional shape. The cross-linking agent may include smaller molecules that have a higher tendency to diffuse through the interface between the different fluid layers in the laminar flow. For example, the cross-linking agent may include hydrogen peroxide ($H_2O_2$), horseradish peroxidase (HRP), calcium chloride, thrombin, water, an enzyme, or the like.

Additional fluid sources, such as fluid source 126, may be provided to supply a sheath (shaping) fluid, or additional polymer precursor fluid(s). An additional polymer precursor fluid may contain a polymer precursor, and may have the same or different contents as another precursor fluid.

Each of the fluids may include a suitable solvent. For example, PBS may be used as the solvent. Water, such as deionized water, may also be used as a solvent.

As depicted in FIG. 1, each fluid source 122, 124, 126 is connected to a respective inlet 112, 114, 116. However, a fluid source may be connected to two of the three inlets 112, 114, 116, depending on the application, as will become clear below. In some applications, two fluid sources such as fluid sources 122 and 124 may be sufficient, and fluid source 126 may be omitted.

A regulator controller 130 may be provided for controlling flow rate regulators 132, 134, 136. Each flow rate regulator 132, 134, 136 is associated with an inlet 112, 114, 116 for regulating the flow rate of the fluid through that inlet 112, 114, 116. Controller 130 may be adapted to control flow rate regulators 132, 134, 136 to adjust the ratio of different flow rates at inlets 112, 114, 116 in order to adjust the size and shape of the fiber formed, as will be further described below. The regulators 132, 134, 136 may be any suitable device or structure that can be controlled to vary the fluid flow rate through inlets 112, 114, 116. For example, valves or fluid pumps may be used as flow regulators.

Optionally, a light source (not shown) may be provided for irradiating the polymerizing section 108 to photo-initiate cross-linking in the fluid low.

Optionally, a heater (not shown) may be provided, such as being incorporated into the wall of polymerizing section 108, for thermal initiating cross-linking in the fluid flow.

Both the light source and heater may be omitted if cross-linking is to be initiated by chemical initiation such as using an enzyme or another chemical agent.

The components of apparatus 100 may be made of any suitable material.

In some applications, apparatus 100 may be operated as follows. The fluid sources 122, 124, 126 are connected to inlets 112, 114, 116 respectively as depicted in FIG. 1.

Depending on the desired fiber construction, different fluids may be selectively injected into spinneret 102 through different inlets 112, 114, 116. For illustration purposes, it is first assumed that a tubular polymer fiber is to be formed. In this case, fluid source 122 may supply the fluid containing the cross-linking agent to inlet 112, fluid source 124 may supply the precursor fluid containing the polymer precursor to inlet 114, and fluid source 126 may supply a sheath fluid to inlet 116.

The fluids from fluid sources 122, 124, 126 are respectively injected into conduit 110 through inlets 112, 114, 116 and connecting section 106 at respective flow rates. The respective fluid flows are directed into conduit 110 by connecting section 106. The flow rates are controlled by controller 130 through flow rate regulators 132, 134, 136. The flow rates of the fluids at inlets 112, 114, 116 and thus in conduit 110 are selected so that the different fluids form a laminar flow 400 in conduit 110, as illustrated by the dashed lines and arrows in FIG. 4, and that the different laminar flow layers, such as flow layers 402, 404, 406, have the desired thickness so that the resulting fiber has a desired cross-sectional shape and size.

Unless otherwise specified, the flow rates refer to flow rates through conduit 110, and the input flow rates refer to flow rates at inlets 112, 114, 116. A flow rate refers to the total amount of a fluid flow flowing through conduit 110 in a unit time. The amount may be measured in, for example, volume, weight, or molar amount. At steady state, the input flow rate for a given liquid is the same as the flow rate for that liquid through conduit 110. Further, the flow rate of one fluid flow through conduit 110 may depend on the input flow rate of that fluid through the corresponding inlet, and the input flow rates of other fluid flows. The volumetric ratios of the different fluid flows inside conduit 110 are dependent on the relative ratio of flow rates of the different fluid flows. As the volume ratio changes, the size and shape of the different fluid flow layers in conduit 110 also change. Thus, by adjusting the input fluid flow rates, the size and shape of the fluid flow layers can be (dynamically) adjusted.

The relationship between flow rates (or input flow rates) and the flow layer dimensions can be estimated based on theoretical calculation for a given embodiment, as can be understood by those skilled in the art. Exemplary equations for calculating the approximate flow diameters based on flow rates are given in Example I below.

Figure 4:
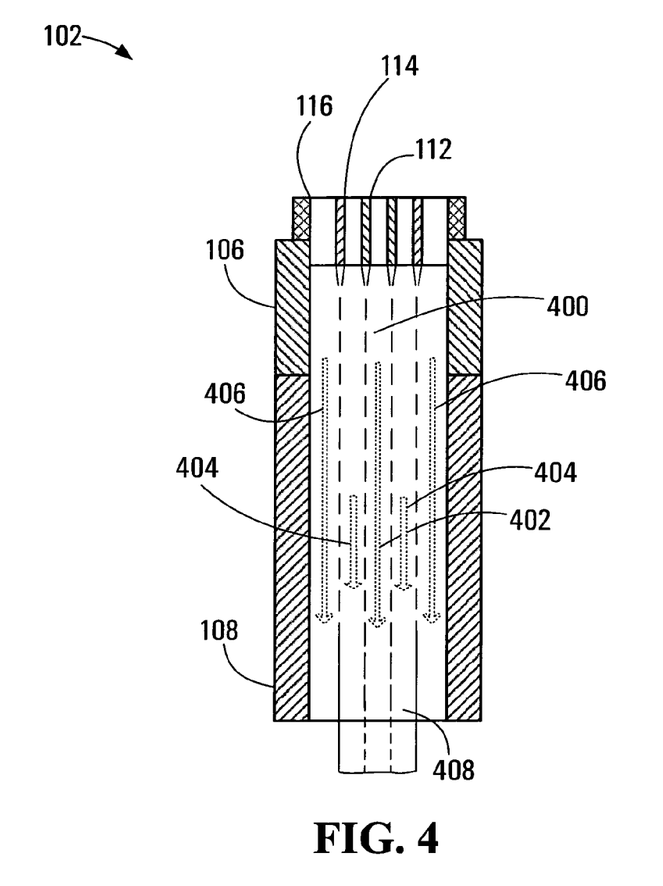
FIG. 4 is a cross-sectional view of the spinneret as in FIG. 3 during operation.

In the laminar flow, the adjacent fluid layers such as layers 402, 404, although in physical contact, will flow at respective flow rates. Some transversal diffusion can occur at the interface region between two adjacent layers but the general dimension of each flow layer can remain substantially unchanged in conduit 110. Therefore, the fluid from fluid source 122 and injected through inlet 112 forms an inner, generally cylindrical layer of fluid flow 402. The fluid from fluid source 124 and injected through inlet 114 forms a middle, generally tubular layer of fluid flow 404 that encloses the inner layer of fluid flow 402. The fluid from fluid source 126 and injected through inlet 116 forms an outer, generally tubular layer of fluid flow 406 that encloses the middle layer of fluid flow 404. Layers of fluid flows 402, 404, 406 form the laminar flow 400.

Figure 5:
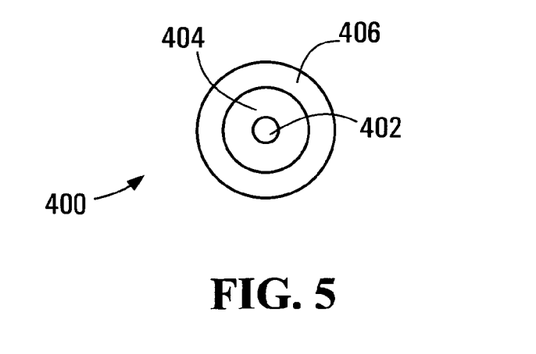
FIG. 5 is cross-sectional view of the coaxial laminar flow shown in FIG. 4.

As can be understood, an interface region between two adjacent flow layers in the laminar fluid flow can be maintained when the two adjacent layers are flowing generally parallel to each other, as can be understood by those skilled in the art. The cross-sectional profiles of fluid layers 402, 404, 406 of laminar flow 400 in conduit 110 are schematically shown in FIG. 5. In this case, the flow velocities in flow layers 402 and 406 may be different or the same.

The fluids, the polymer precursor and the cross-linking agent should be selected so that, as the laminar fluid flow 400 flows through conduit 110, the polymer precursor molecules in the middle layer of fluid flow 402 are substantially prevented from diffusing away from the middle layer, but the molecules of the cross-linking agent are allowed to diffuse from inner layer of fluid flow 402 into middle layer of fluid flow 404. Thus, polymerization by cross-linking of the polymer precursor will occur within middle layer 404 but little polymerization reaction will occur in the inner layer 402 or outer layer 406. As a result, the polymer layer (fiber) formed from the polymerization reaction will have a cross-section generally corresponding to the cross-section of the middle layer 404. If the transverse diffusion rate of the cross-linking agent is too slow, the polymer layer will not form fast enough in the conduit 110. If the transverse diffusion rate of the polymer precursor is too fast, substantial polymerization will occur outside the middle layer 404, it will be difficult to control the cross-section of the formed polymer layer.

The cross-linking reactions may occur when the cross-linking agent comes into contact with, or near, the polymer precursor in the middle layer 404. The reactions may be accelerated or initiated using any suitable technique.

For example, the cross-linking reactions in the middle layer of fluid flow 404 may be initiated by a suitable initiation method, such as chemical initiation, photo-initiation, or thermal initiation. For example, chemical initiation may be effected by including a chemical agent such as a suitable enzyme in middle layer 404 or in an adjacent layer. Photo-initiation may be effected by irradiating the fluids in conduit 110 with laser or ultraviolet light. Thermal-initiation may be effected by heating or cooling the fluids in conduit 110 such as with a heater (not shown).

As the polymer precursor molecules are cross-linked by cross-linker molecules, a polymer, such as a hydrogel, is formed in middle layer of fluid flow 404. As middle layer 404 has a generally tubular cross-section, the polymer forms a generally tubular polymer fiber 408, which has a cross-section profile corresponding generally to the cross-section of middle layer of fluid flow 404. In this case, a generally tubular polymer fiber 408 is formed. The inner diameter of fiber 408 is similar to the diameter of inner layer of fluid flow 402 (or the inner diameter of middle layer of fluid flow 404). The outer diameter of fiber 408 is similar to the outer diameter of middle layer of fluid flow 404 (or the inner diameter of outer layer of fluid flow 406).

As fiber 408 emerges from conduit 110 of spinneret 102, it may be solidified (cured) by air or in a liquid such as in liquid bath 120 shown in FIG. 1. Fiber 408 may have a porous structure.

The non-polymerized layers of fluid flows, in this case layers 402 and 406, will exit conduit 110 in fluid form, and may be received by liquid bath 120.

As can be appreciated, a similar fiber 408 may be obtained if both fluid sources 122 and 126 supply the cross-linking agent fluid.

Alternatively, if both fluid sources 122 and 124 supply precursor fluid(s) and fluid source 126 supplies the cross-linking agent fluid, a two-layer cylindrical polymer fiber will be formed, with a diameter substantially corresponding to the outer diameter of middle layer 404 (or the inner diameter of outer layer 406). If the fluid sources 122 and 124 supply different precursor fluids that contain different other contents, such as with different cell loadings or different concentrations of certain ingrespinneretnts, the two layers of the fiber will have different contents or structures. For example, the two fiber layers may have different cell loadings or different physical or chemical properties depending on the difference in the precursor fluids.

In a further alternative, one of the inlets may be closed, and a two-layer laminar flow may be formed from the two input fluids injected through the two open inlets.

By adjusting the flow rates at inlets 112, 114, 116, the cross-sectional shape and size of the resulting fiber can be conveniently changed, without changing the physical dimensions of spinneret 102. As the flow rates of the different fluids may be changed during spinning of a single fiber, the single fiber may have a varying diameter.

The diameters of the fibers may be conveniently varied on the order of micrometers. For example, a tubular fiber may have an inner diameter of about 20 µm or larger, and an outer diameter of about 60 µm or larger. A cylindrical fiber may have a diameter of about 20 µm or larger.

It is also convenient to incorporating cells in the resulting fiber, by dispersing the cells in the corresponding fluid(s) from which the polymer fiber is formed. For example, cells may be included in the precursor fluid, the cross-linking agent fluid, or the sheath fluid. After the fiber is formed and solidified, the cells are immobilized in the fiber. Depending on in which fluid flow the cells are initially dispersed, the cells may be immobilized throughout the fiber, or concentrated on the inner or outer surface regions of the fiber.

To keep the cells healthy and to allow them to grow, a cell culturing medium may also be included in the fluid(s) in which the cells are dispersed. For example, a cell culture medium may be included in the precursor fluid.

Figure 6:
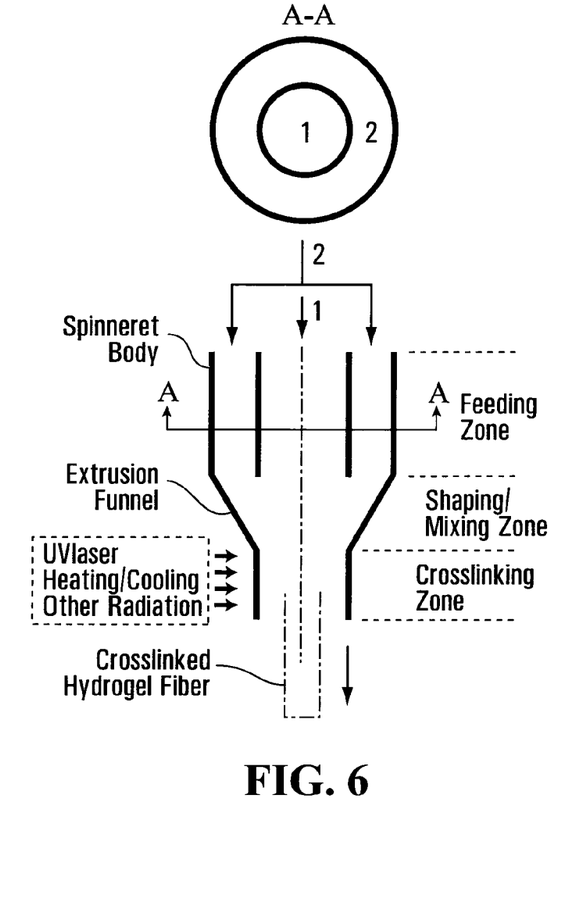
FIGS. 6, 7, 8, and 9 are partial cross-sectional views of alternative spinnerets with different numbers of nested tubular inlets.
Figure 7:
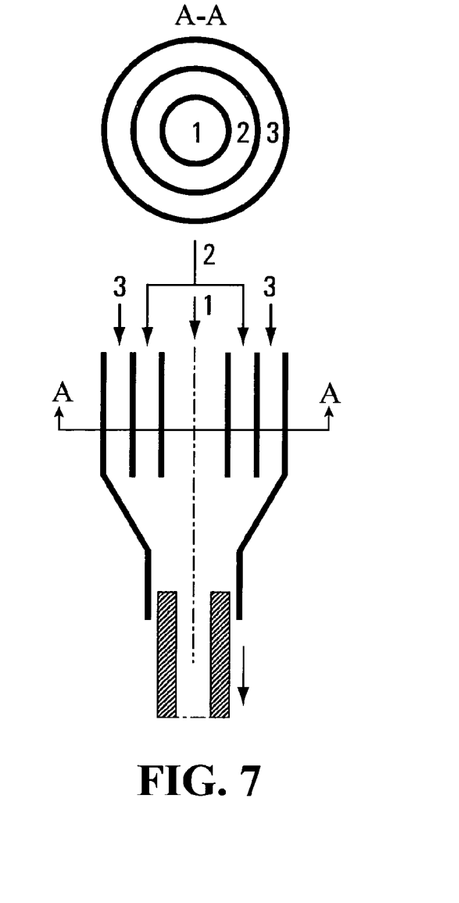
Figure 8:
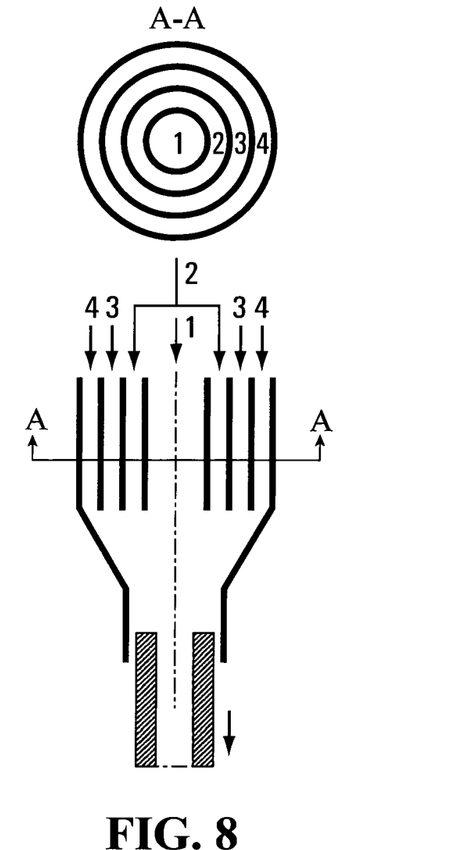
Figure 9:
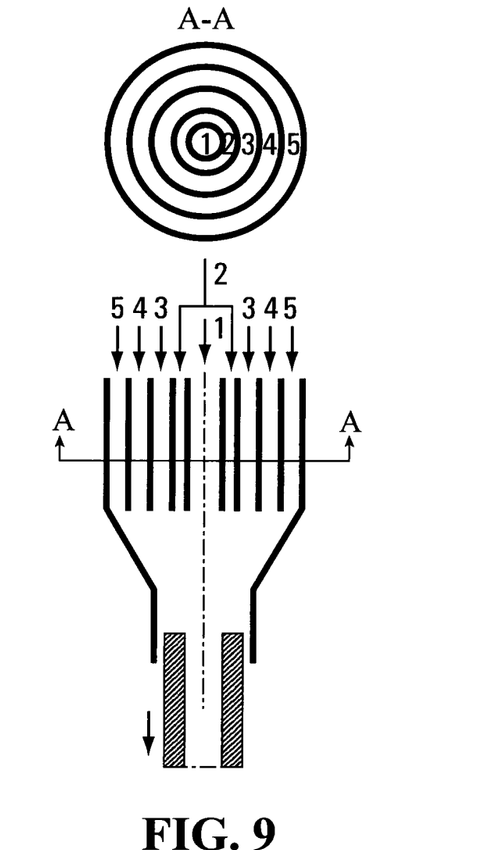
Figure 10:
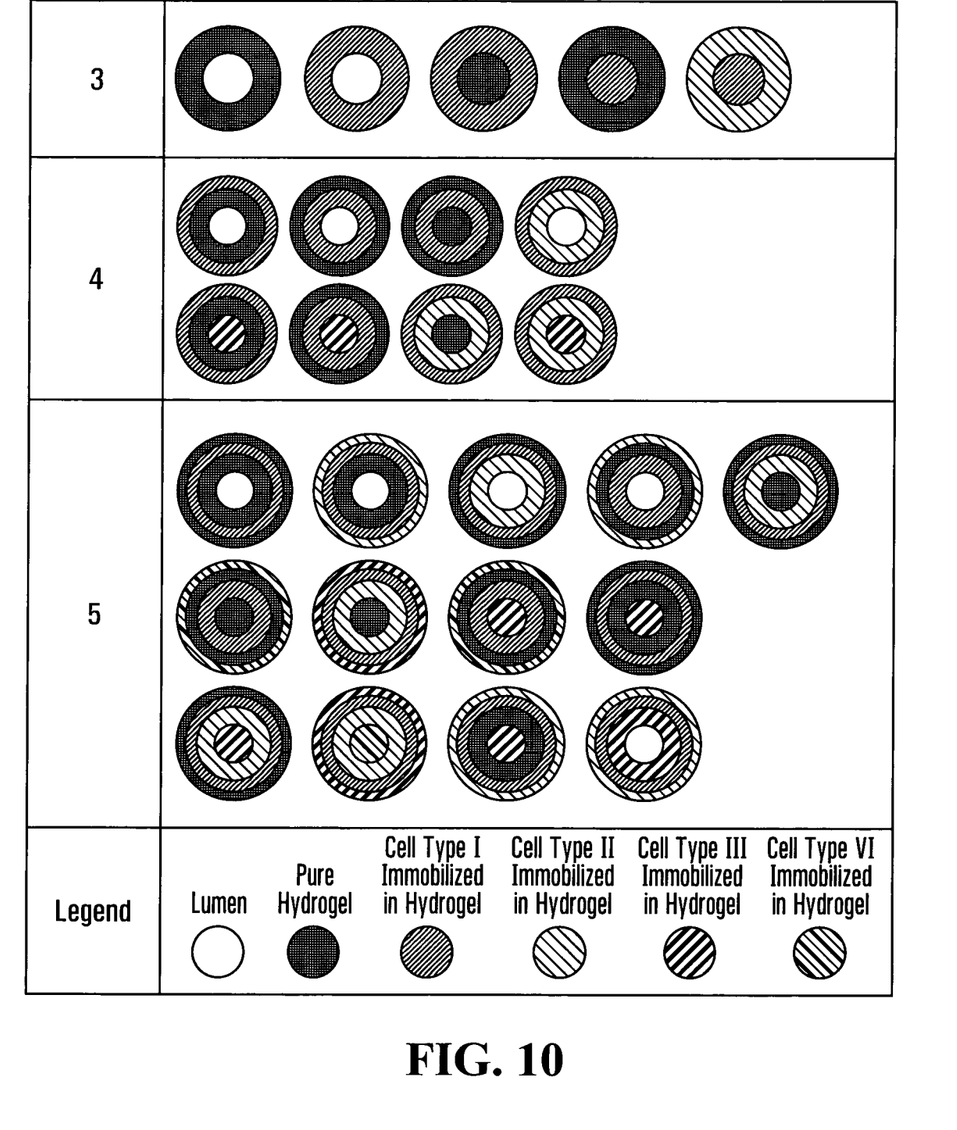
FIG. 10 is a table showing representative cross-sectional constructions of polymer fibers that can be formed using the spinnerets of FIGS. 7, 8, and 9.

The exemplary embodiments disclosed herein may be modified. For example, the spinneret may be modified to include more nested tubular inlets than shown in FIGS. 2 and 3. For example, more inlets may be nested for forming multi-layer fibers. Some possible alternative inlet sections are illustrated in FIGS. 6, 7, 8, and 9, which have 2, 3, 4, and 5 nested tubular inlets respectively, and a generally funnel shaped connecting section. While a two-inlet construction (as shown in FIG. 6) may be used to form a cylindrical or tubular fiber, with three or more nested inlets, multi-layer fibers may be conveniently formed, as can be understood. Further, with more than two nested inlets, it is more convenient to adjust the sizes and shapes of the layers of the fluid flows and thus the resulting fibers. In a multi-layer fiber, one or more of the layers may contain cells. Different fiber layers may contain different types of cells or different concentrations of cells. To illustrate, some exemplary fiber cross-section patterns are shown in FIG. 10, where the number on the left column of each row indicates the number of nested inlets of the extrusion head.

Fibers with different cross-sectional shapes may be obtained by modifying the cross-sectional shapes of the conduit and the inlets. For example, the cross-sectional profiles of the conduit or inlets may be generally circular, oval, rectangular, square, or triangular.

The polymer in the fiber may be any suitable polymer. For example, for biological or tissue engineering applications, the polymer may be biocompatible with the other cells or tissues involved in the application. The polymer may be initially formed in a gel form.

Various suitable hydrogel precursors may be used as the polymer precursor. The hydrogel precursor may be cross-linked by any suitable cross-linking method. For example, cross-linking of a suitable hydrogel precursor may be chemically initiated, which may involve radical polymerization, chemical reaction, irradiation, or an enzyme. Cross-linking of the hydrogel precursor may also be physically initiated, which may involve ionic interaction, crystallization, amphiphilic block and graft copolymers, hydrogen bonds, protein interactions, or variation in temperature or pH.

Conveniently, other materials and agents may also be incorporated into the fibers with the cells. For example, other biological components, such as growth factors, extracellular matrix (ECM) materials, drugs, proteins, or nutrients, may also be included in the fluid flow and be incorporated into the fiber.

A hydrogel fiber may be formed from a blend of two or more polymer materials, such as a mixture of alginate and Gtn-HPA. With a blended fiber one of the polymer materials may be selectively removed after fiber formation, thus increasing the porosity of final fiber.

In order to immobilize cells on the internal surface of the lumen of a tubular fiber, a diluted cross-linker solution may be added to the inner fluid flow that also contains the cells. The formed hollow fiber may be periodically compressed to seal the cells on to the inner fiber wall. In some applications, if the fiber is not periodically compressed the cells in the lumen may not be sealed and may be washed away by the flow.

Tubular hydrogel fibers formed according to an exemplary disclosed herein may be useful for many applications. In tissue engineering, the tubular fibers may be used as tubular scaffolds, such as for reconstructing tissues that provide a function of ureter, bladder, urethra, artery, peripheral nerve, liver, kidney, or lung.

For example, narrowed coronary artery can lead to reduction in coronary blood flow rate and cause myocardial infarction. A possible clinical treatment of this coronary artery narrowing is coronary artery bypass graft (CABG), where the blocked artery is bypassed through either the patient's internal mammary artery or the saphenous vein. A tubular fiber loaded with appropriate cells may be used for this purpose. Conveniently, the cell loaded fiber may be prepared in a single extrusion process.

The polymer fibers may be used in the fabrication of artificial blood vessel grafts, nerve conduits, kidney tubules, as well as three-dimensional (3D) cell culture structures. The fibers may be seeded with cell to form cell-seeded hydrogel tubular scaffolds and cell-seeded hydrogel filaments.

The polymer fibers may also be used as vascular constructs, nerve conduits, kidney tissue, or other types of artificial tissues or scaffolds.

As it is possible to simultaneously form a composite fiber layer and uniformly embed cells in the layer on the inner surface of a hollow fiber, such composite fibers may have applications for forming bioreactors, bio-artificial organs, and water treatment cartridges, or the like.

As the shape of the fiber can be dynamically modified by varying the flow rates, the process may be referred to as a "hydrodynamic shaping" process, and the extrusion process may be referred to as "hydrodynamic co-extrusion."

EXAMPLES

The materials used in the Examples were obtained as follows unless otherwise specified.

Gelatin (8-14 kDa), horseradish peroxidase and $H_2O_2$ (31 wt %) were purchased from Wako™ (Osaka, Japan), Tokyo Kasei Kogyo Co. (Tokyo, Japan) and MGC Pure Chemicals™ (Singapore), respectively.

4'-6-Diamidino-2-phenylindole (DAPI) was obtained from Invitrogen Corp. (California, USA).

Artisan™ Hematoxylin and Eosin (H&E) stain kit was purchased from Dako™ (California, USA). PKH2 Green Fluorescent Cell Linker Kit for General Cell Labeling (PKH2-GL) and PKH26 Red Fluorescent Cell Linker Kit for General Cell Labeling (PKH26-GL) were obtained from Sigma-Aldrich™ (Singapore).

Live/dead viability/cytotoxicity assay kit for mammalian cells (containing calcein and EthD-1) was purchased from Invitrogen Corp. (California, USA).

All chemicals were used without further purification.

Example I

Figure 11A:
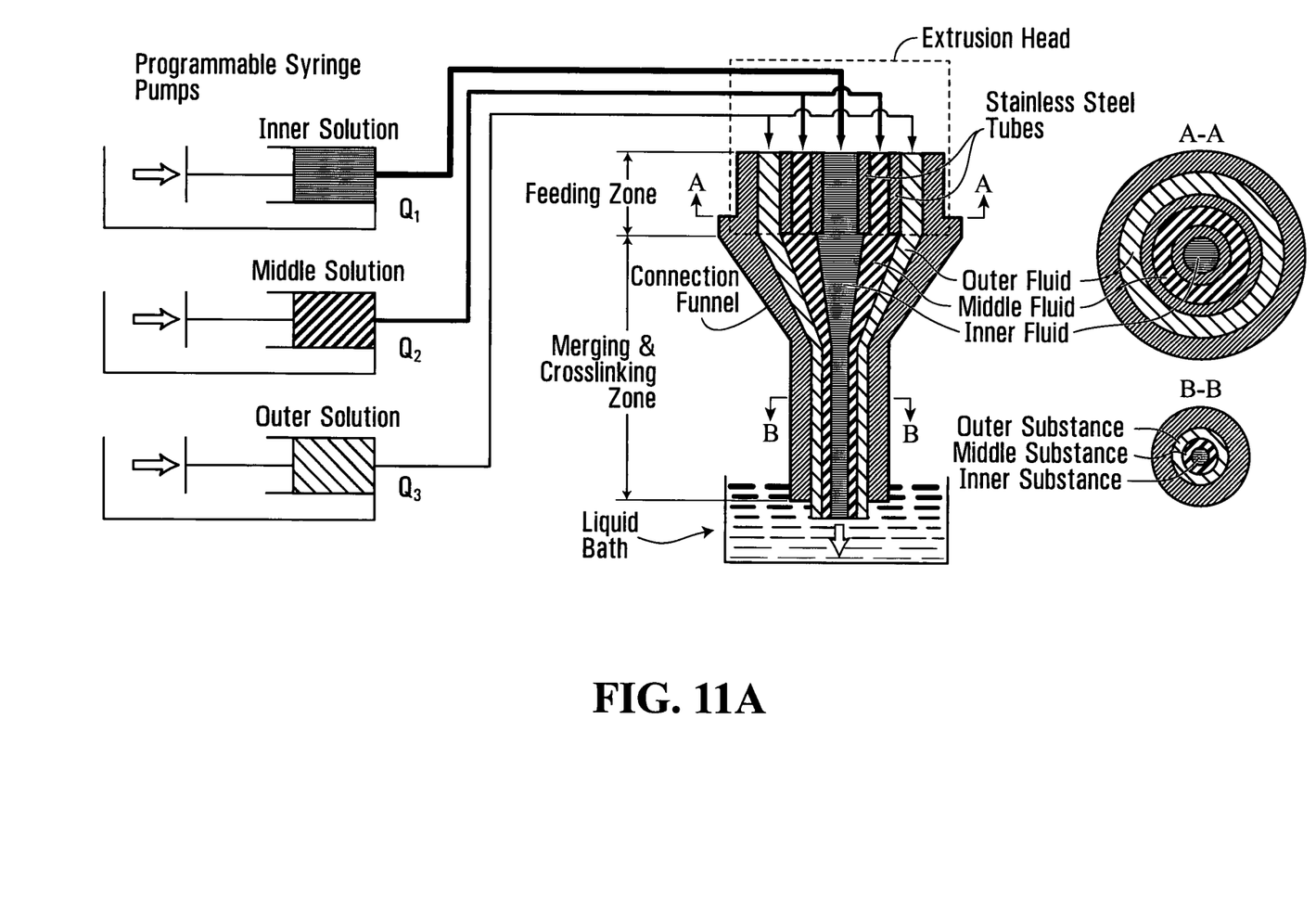
FIG. 11A is a schematic diagram showing a spinning apparatus used in the Examples.

A hydrodynamic spinning system was formed using spinneret with a triple-orifice inlet section, as schematically illustrated in FIG. 11A. The inlet section of the spinneret included three cylindrical stainless steel tubes nested coaxially within a jig orifice. Five holes were formed in a flange of the inlet section of the spinneret, one holes located at the center and four holes located along the periphery of the inlet section. The spinneret had a single outlet orifice. A fluid conduit extended from the inlet holes to the outlet orifice.

Two needles (18G and 25G) with blunt tips were inserted into the inlet holes and extended into the gaps between the respective steel tubes, which formed three concentric orifices.

The jig held the nested tubes in position and connected the three concentric orifices to respective flow channels. The flow rate of fluid through each flow channel was controlled with a programmable controller, and could be varied during operation.

The outlet orifice had a 1.7-mm inner diameter.

The spinneret held the needles in position, and connected the three concentric annulus/orifices individually to the programmable syringe pumps. Coaxially attached to the orifices of the spinneret was a connection funnel through which the liquids from the three concentric orifices were first merged and then discharged to the liquid bath. The straight part of the funnel was a glass capillary with an inner diameter of 0.78 mm and a length of 15 mm. The connection funnel connected the inlet section (concentric orifices) to the conduit section.

When the different solutions were pumped through the three (inner, middle and outer) inlets (orifices), the fluids at low Reynolds numbers merged in the connection funnel and formed a triple-layered coaxial laminar flow.

Liquids from the three concentric orifices were injected into the conduit section and the formed fiber was discharged into a liquid bath.

During the spinning operation, sheath fluid(s) was injected into the polymerization conduit through the inner orifice or the outer orifice, or both. A solution comprising a hydrogel precursor was injected into the conduit through the middle orifice. A cross-linker solution is included in the sheath fluid through either or both of the inner and outer orifices.

Figure 11B:
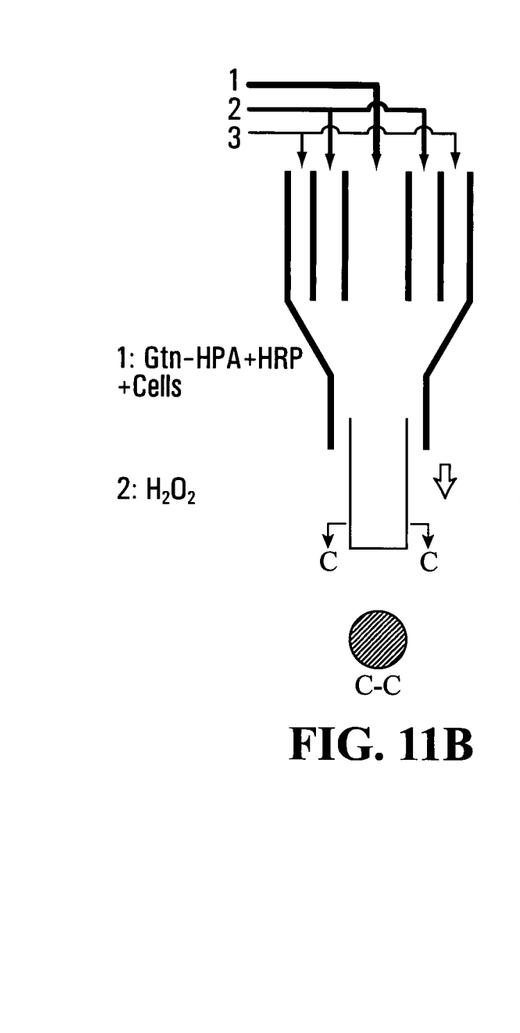
FIGS. 11B, 11C, and 11D are schematic diagrams showing different fluid layer patterns used in the Examples.
Figure 11C:
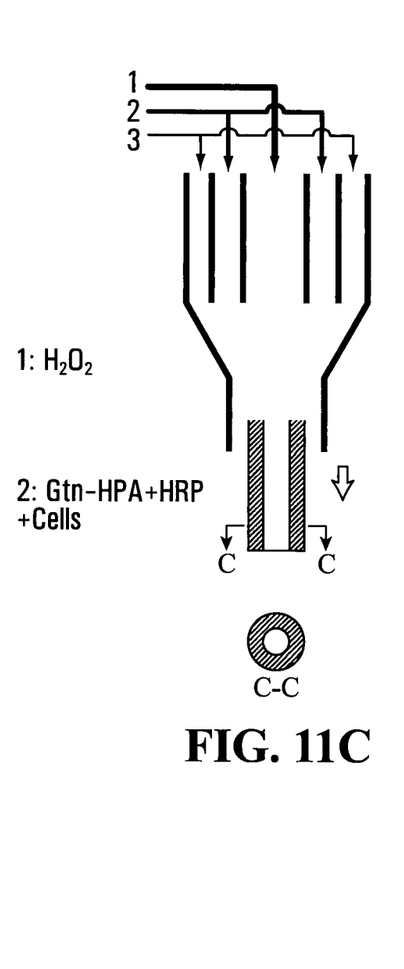
Figure 11D:
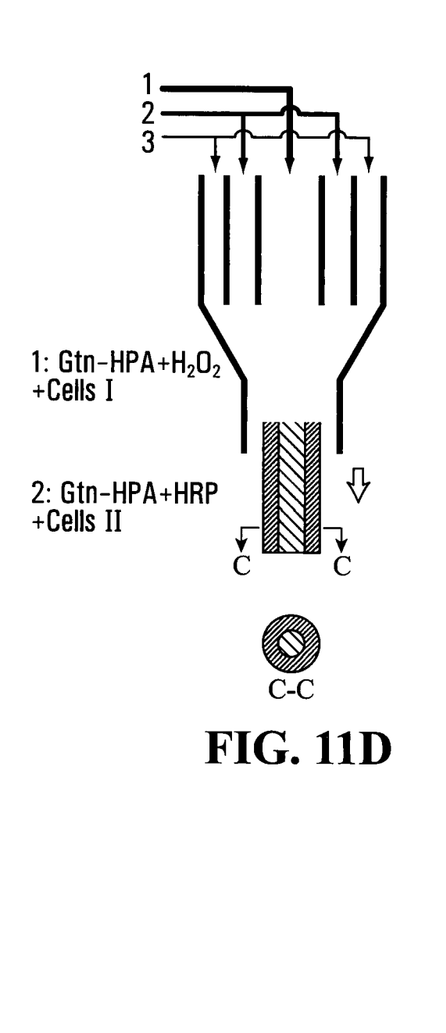

Representative combinations of fluid input schemes are illustrated in FIGS. 11B, 11C, and 11D.

The dimension of the flow profiles and the fiber were predicted based on the spinneret dimensions and the flow rates. Assuming the diameter of the conduit is $D_R$, the inner diameter ($D_I$) and the outer diameter ($D_O$) of the middle tubular layer in the laminar flow were calculated as $$D_I = \sqrt{1 - \sqrt{\frac{Q_2 + Q_3}{Q_1 + Q_2 + Q_3}}} \times D_R \quad (1)$$

$$D_O = \sqrt{1 - \sqrt{\frac{Q_3}{Q_1 + Q_2 + Q_3}}} \times D_R \quad (2)$$

where $Q_1$, $Q_2$ and $Q_3$ respectively denote the input flow rates through the inner, middle and outer orifices of the inlet section. The flow rates were controlled by pre-setting the syringe pumps that drove the fluid flows.

Compared to the small cross-linker molecules, the transverse diffusive broadening of the hydrogel precursor was negligible in the multi-layer coaxial laminar flow. In addition, the cross-linking began at the interfaces of different flow layers, which further reduced the possibility of transverse diffusion of the hydrogel precursor into the inner or outer layers.

Therefore, the diameters of the polymer tubular fiber were approximately the same as those of the middle laminar layer.

A 1×PBS solution was used for the liquid bath.

Example II

Polymer fibers were formed using the spinneret of Example I. The polymer precursors used include Gtn-HPA, calcium alginate, and polysulfone. The cross-linking method used was enzymatic oxidative reaction, ionic interaction, or phase inversion.

Gtn-HPA conjugates were synthesized by a general carbodiimide/active estermediated coupling reaction (see Example VI below). They were cross-linked by enzymatic oxidative reaction of HPA moieties using $H_2O_2$ and horseradish peroxidase (HRP). The oxidative coupling of phenol proceeded at the C—C and C—O positions between phenols.

Pure Gtn-HPA fibers, cell-seeded single-layered fibers, and cell-seeded two-layered fibers were prepared. For cell-seeded samples, cells were cultured in the precursor solution. It was found that the cells were not damaged during fiber formation. In this example, the stiffness of the hydrogel and the gelation time may be conveniently controlled by varying the $H_2O_2$ and HRP concentrations.

Example IIA (Pure Gtn-HPA Fibers)

Gtn-HPA powder was dissolved in PBS at concentrations ranging from 12.5 mg/ml to 50 mg/ml. HRP was then added to the Gtn-HPA solution, resulting in an HRP concentration of 6.25 units/ml. Next, a high concentration solution of $H_2O_2$ (31 wt %, MGC Pure Chemicals Pte. Ltd., Singapore) was diluted with deionized (DI) water to yield a diluted $H_2O_2$ solution with a $H_2O_2$ concentration of 0.5 wt %.

DI water, the Gtn-HPA/HRP solution and the diluted $H_2O_2$ solution were separately loaded into three syringe pumps, and were pumped into the inlet orifices of the extrusion head. Depending on how the solutions were supplied to the inlet orifices, both tubular and cylindrical hydrogel fibers were prepared.

Different tubular hydrogel diameters were obtained by varying the ratio of input flow rates, without changing the dimensions of the spinneret.

Figure 12:
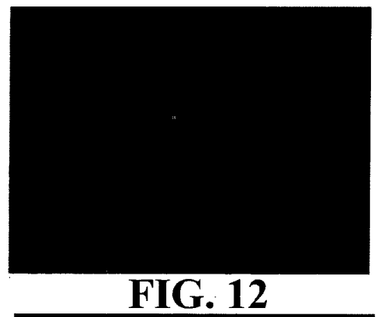
FIGS. 12, 13, 14, and 15, 16, and 17, 18, and 19 are images of sample fibers.
Figure 13:
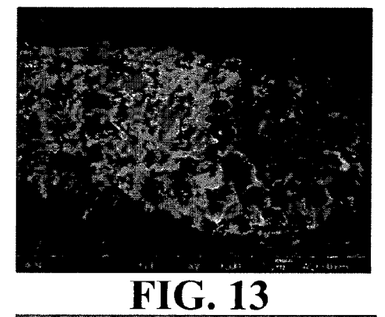
Figure 14:
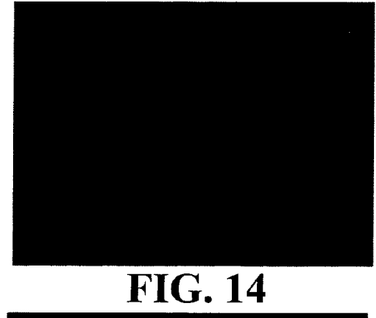
Figure 15:
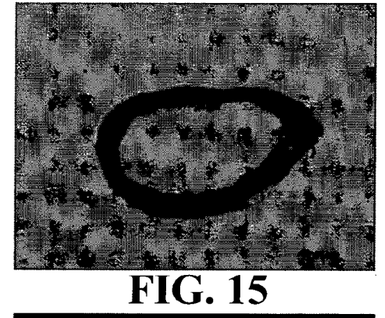

Representative images of tubular and cylindrical sample fibers are shown in FIGS. 12, 13, 14, and 15. The optical images in FIGS. 12 and 14 were taken when the Gtn-HPA fibers were immersed in water. FIGS. 13 and 15 show cryosectional images of sample Gtn-HPA fibers. The fibers were first fixed by a tissue embedding medium (Tissue-Tek™), and then sectioned by a cryostat (LEICA CM3050S). The cryosections were stained with hematoxylin/eosin.

FIG. 12 shows an optical image of sample solid fibers formed of pure Gtn-HPA hydrogel. The solid fibers were porous as shown in FIG. 13, which is a scanning electron microscopy (SEM) imaged obtained after freeze drying and cutting the sample fiber. The sample fibers shown were formed with an inner hydrogel precursor (Gtn-HPA+HRP) flow rate of 5 μl/min, a middle $H_2O_2$ flow rate of 20 μl/min, and an outer 1×PBS flow rate of 75 μl/min. The Gtn-HPA solid fibers were transparent in DI water with substantially uniform diameters.

FIG. 14 shows an optical image of sample hollow fibers formed of pure Gtn-HPA hydrogel. Both the lumen and the wall of the fibers were visible in the image. The sample fibers shown were formed with an inner $H_2O_2$ flow of 15 μl/min, a middle hydrogel precursor (Gtn-HPA+HRP) flow of 35 μl/min, and an outer DI water flow of 50 μl/min. In the middle precursor flow, the Gtn-HPA concentration was 25 mg/ml, and the HRP concentration was 6.25 units/ml. The inner $H_2O_2$ flow contained 0.5 wt % of $H_2O_2$. The inner and middle flows were 1×PBS solution based. As can be seen in FIG. 15, the cross-section of the sample fiber is generally annular.

Sample Gtn-HPA hydrogel fibers were found to be mechanically strong and elastic. Sample fibers of a 20 μm diameter could be handled without breakage.

Example IIB (Cell-Seeded Fibers)

For co-extrusion of cell-seeded single-layered fibers, a suspension of isolated Madin-Darby canine kidney (MDCK) cells was uniformly mixed with the Gtn-HPA/HRP solution at concentrations ranging from $10^5$ cells/ml to $10^7$ cells/ml. The cells were added to the Gtn-HPA/HRP solution before it was loaded into the syringe pump. The isolated cells can also be added to the Gtn-HPA solution at the inlet section via an additional syringe pump. Through this pump, a cell suspension can be injected into the Gtn-HPA/HRP solution just before it was fed into the triple-orifice spinneret.

In this example, the shaping fluid and the liquid bath used were 1×PBS or a cell culture medium DMEM (Dulbecco's Modified Eagle's Medium) to maintain the cell viability in an isotonic condition.

FIGS. 16, 17, 18, and 19 show representative images of the sample cell-seeded, single-layered Gtn-HPA hydrogel fibers.

Figure 16:
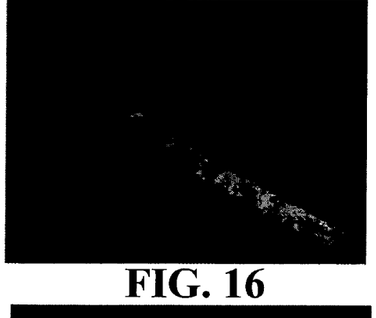
Figure 17:
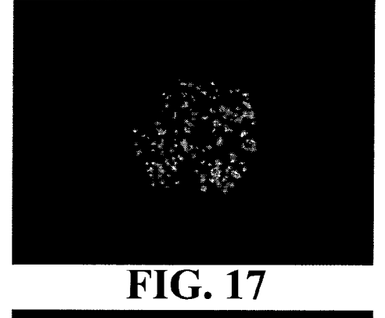

FIGS. 16 and 17 show solid sample fibers. The sample fibers were formed with an inner hydrogel precursor (Gtn-HPA+HRP+MDCK cells) flow rate of 7.5 μl/min, a middle $H_2O_2$ flow rate of 17.5 μl/min, and an outer 1×PBS flow rate of 75 μl/min. A MDCK cell suspension was added to and uniformly mixed with the Gtn-HPA+HRP solution prior to the loading of this precursor solution into the syringe pump. The optical micrograph (FIG. 16) and cryosection image (FIG. 17) showed that MDCK cells were distributed uniformly within the hydrogel fibers.

Figure 18:
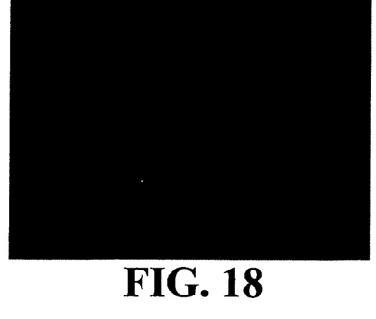
Figure 19:
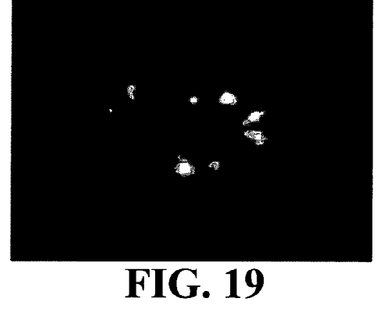

FIGS. 18 and 19 show tubular sample fibers. The fluids used were similar to those used for the samples shown in FIGS. 12, 13, 14, and 15, with addition of the MDCK cells at the concentration of $10^6$ cells/ml. The cryosectional images in FIGS. 17 and 19 were obtained by staining the sample with DAPI. These sample fibers were obtained by switching the inner and middle flows described above. Specifically, these sample hollow fibers were formed with an inner $H_2O_2$ flow rate of 2.5 μl/min, a middle hydrogel precursor (Gtn-HPA+HRP+MDCK cells) flow rate of 7.5 μl/min, and an outer 1×PBS flow rate of 90 μl/min. The different layers in the sample filers could be discerned by histology.

Example IIC (Cell-Seeded, Two-Layered Fibers)

For extrusion of cell-seeded, two-layered fibers, a high concentration $H_2O_2$ solution was directly added to a portion of the Gtn-HPA solution (without being first diluted with DI water) at concentrations ranging from 0.01 wt % to 0.25 wt %. As MDCK cells could only withstand less than about 0.25 wt % of $H_2O_2$ for an extended period of time, the $H_2O_2$ concentration was reduced. The $H_2O_2$-containing Gtn-HPA solution was fed to the inner orifice of the inlet section. A HRP-containing Gtn-HPA solution was prepared as in Example IIB and was fed to the middle orifice. When the two solutions were injected into the conduit of the spinneret, cross-linking of Gtn-HPA hydrogel occurred at the interface region between the two laminar flow layers, as both $H_2O_2$ and HRP diffused transversally into the other layer.

Cell pellets were dispersed into the inner Gtn-HPA flow, or the middle Gtn-HPA flow, or both, depending on in which layer(s) the cells were to be seeded.

Two-layered hydrogel fibers with seeded cells were formed. The dual-layer structures of the sample fibers were verified with optical images and cryosectional images. These sample fibers were cylindrical (solid) as the polymer precursor in the inner Gtn-HPA flow was also cross-linked during the spinning process.

Both MDCK cells and Human microvascular endothelial (HME) cells were also immobilized in the same hydrogel fibers, with HME cells lining the periphery and MDCK cells occupying the core. These sample fibers were formed with an inner hydrogel precursor (Gtn-HPA+$H_2O_2$+MDCK cells) flow rate of 15 μl/min, a middle hydrogel precursor (Gtn-HPA+HRP+HME cells) flow rate of 12.5 μl/min, and an outer 1×PBS sheath flow rate of 72.5 μl/min. In this case, the solution with Gtn-HPA+$H_2O_2$+MDCK cells replaced the function of 1×PBS-diluted $H_2O_2$ solution in the previous example of hollow fiber extrusion. When merged with the solution containing Gtn-HPA+HRP+HME cells from the middle orifice, cross-linking of the double-layered Gtn-HPA hydrogel fibers occurred at the flow interface via the transverse diffusion of both $H_2O_2$ and HRP.

In some tests, to distinguish between the different types of cells, the HME cells and MDCK cells were labeled with fluorescent cell linkers, PKH2-GL and PKH26-GL, respectively, which incorporated reporter molecules onto the cell membrane. It was observed that these labeled cells retained their biological and proliferation activities. Thus, cell tracking was conducted with ease.

Example III

To evaluate cell viability, cell-seeded sample hydrogel fibers were incubated in DMEM. A monolayer of MDCK cells was found to form on the surface of the fiber after four days of culture. The cells within the fiber also grew larger. The morphology of the cells in (or on the surface of) the hydrogel fiber depended not only on the hydrogel composition, but also on the type of cells involved. Attachment and growth of other types of seeded cells on the fiber surface were also observed.

Cells were also cultured in the lumen of sample pure Gtn-HPA hollow fibers. The diameter of the lumen of the tested sample fiber was less than about 100 µm. Cell growth with the lumen was observed.

To evaluate the influence of the immobilization process on cell viability, cell-seeded sample hydrogel fibers were collected from the liquid bath and were divided into two portions. One portion was analyzed using live/dead assay, while the other portion was incubated in a cell culture medium. The live/dead assay of cells embedded in the matrices of the Gtn-HPA hollow fibers showed that more than 95% of the cells survived the in situ cross-linking process. This confirmed that the enzymatic cross-linking of Gtn-HPA hydrogel was a mild chemical reaction and was not cytotoxic.

MDCK cells were found to proliferate well within the single-layered Gtn-HPA fibers, forming a monolayer on the hydrogel surface after 4 days of incubation. Similar results were observed in the NIH/3T3-seeded single-layered Gtn-HPA fibers after 10 days of incubation in DMEM. The proliferation of cells and formation of monolayer were also observed for the hollow Gtn-HPA fibers seeded with HME cells and human proximal tubular (HPT) cells after 8 days of incubation in epithelial growth medium (EGM) and renal epithelial growth medium (REGM) supplemented with 0.5% (v/v) penicillin/streptomycin (100 units/nil), respectively.

The morphology of the cells in (or on the surface of) the hydrogel fibers depended on the type of cells immobilized. The presence of the RGD sequences in gelatin and the porosity in the hydrogel was found to promote the attachment and proliferation of mammalian cells in these systems.

Example IV Alginate and Alginate/Gtn-HPA Fibers

Pure alginate hollow fibers and blended alginate/Gtn-HPA solid fibers were formed with the apparatus of Example I. For pure alginate hollow fiber extrusion, sodium alginate in the powder form (alginic acid, sodium salt, Sigma Aldrich™, Singapore) was used. Different weight percentages of alginate were dissolved in two different media, DI water and DMEM. Alginate sterilization was achieved by autoclaving (at 121° C. for 20 min) or by gamma irradiation. Before loading into the syringe pump, the alginate solution was filtered to remove yellow precipitates formed over time. Calcium chloride (CaCl2) was used as the gelling agent for alginate. Various concentrations of CaCl2 (50 mM, 100 mM and 200 mM) in DI water were prepared.

To spin alginate/Gtn-HPA blended solid fibers, the above alginate solution was first mixed with the Gtn-HPA/HRP solution. Separately, the $H_2O_2$ solution was diluted with CaCl2 solution. Next, the two solutions were individually loaded into the syringe pumps, and pumped thorough the triple-orifice spinneret.

The hollow structures of the produced fibers were confirmed by microscopic imaging.

Example IV Polysulfone/Gtn-HPA/Cell Fibers (Composite Hollow Fibers)

Polysulfone hollow fibers were formed using the apparatus of Example I, with the inner surface coated with cell-loaded Gtn-HPA hydrogel. First, polysulfone (Sigma Aldrich, Singapore) was dissolved in N-methyl-2-pyrrolidone (NMP) (Sigma Aldrich, Singapore) at concentrations ranging from 5 wt % to 20 wt %. The polysulfone solution was then loaded into the syringe pump that was connected to the outer orifice of the spinneret. Next, a suspension of isolated human proximal tubular cell (HPTC) pellets was uniformly mixed with the Gtn-HPA/HRP solution at concentrations ranging from $10^5$ cells/ml to $10^7$ cells/ml. A blend of Gtn-HPA/HRP/cells was loaded into the second syringe pump connected to the middle orifice of the spinneret. The diluted $H_2O_2$ solution was loaded into the third syringe pump connected to the inner orifice of the spinneret. Unlike in the previous Examples, the formed fibers in this Example were exposed to air before they reached the liquid bath (1×PBS). The formed composite fibers were immediately washed and soaked in a large portion of 1×PBS solution to remove the residual NMP solvent in the fiber. After cutting into appropriate lengths, the washed composite polysulfone fibers were cultured in REGM. It was observed that HPTC cells were fully attached to the fiber surface after 10 days of incubation.

Example VI Synthesis of Gtn-HPA Conjugates

Figure 20:
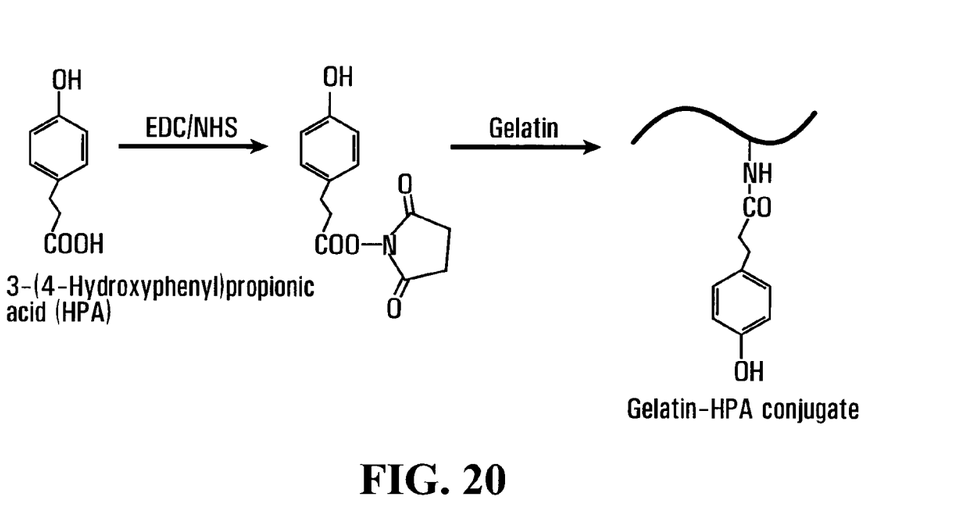
FIGS. 20 and 21 are diagrams of chemical reactions occurred in the production of some sample fibers.

Gtn-HPA conjugates were synthesized by a general carbodiimide/active estermediated coupling reaction, as shown in FIG. 20.

3,4-HPA (3.32 g, 20 mmol), N-hydroxysuccinimide (NHS; 3.2 g, 27.8 mmol) and 1-ethyl-3-(3-dimethylaminopropyl)-carbodiimide (EDC; 3.82 g, 20 mmol) were dissolved in 250 ml of water and dimethylformamide (3:2 volume mixture). The reaction was conducted at room temperature and a pH of 4.7 for 5 hours. Upon completion, 10 g of gelatin in 150 ml of water were added to the reaction mixture, and stirred overnight at room temperature and pH 4.7. The mixture was then extensively dialyzed against 100 mM of NaCl solution, 25% ethanol and water in sequence for 1 day each, and lyophilized. The percentage of amine groups of gelatin introduced with HPA (i.e. degree of conjugation) was determined by the conventional 2,4,6-trinitrobenzene sulfonic acid (TNBS) method to be 90%. The yield was 7.0 g.

Figure 21:
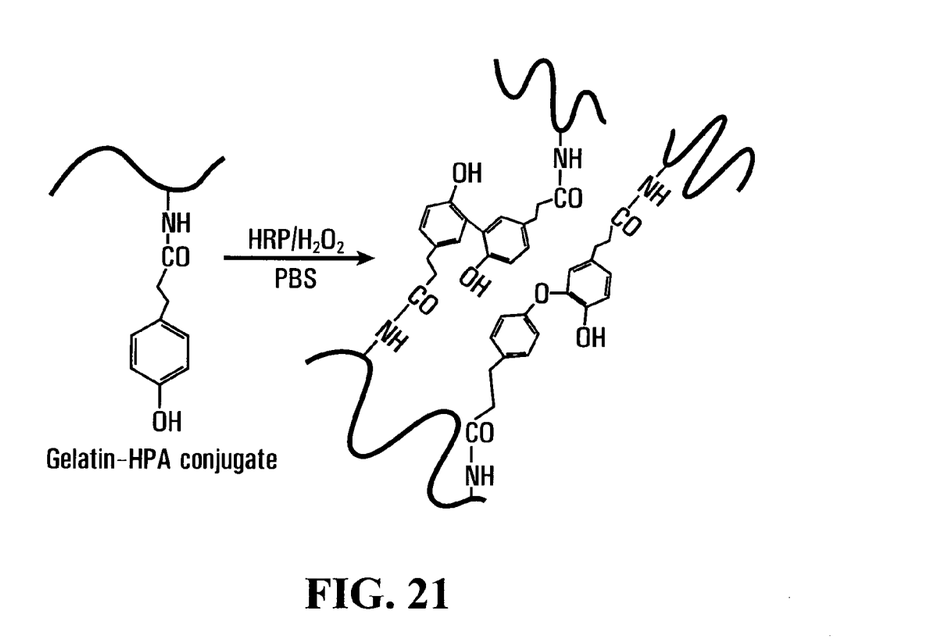

The Gtn-HPA conjugates were cross-linked through an enzymatic oxidative reaction of HPA moieties using HRP and $H_2O_2$, as shown in FIG. 21.

Example VII Characterization of Hydrogel Fibers

An inverted Olympus IX71 optical microscope equipped with a DP70 digital color camera was employed to study the surface morphology and cryosections of the hydrogel fibers incorporated with or without cells.

Fluorescent imaging of dual-layered solid fibers and live/dead assay of the immobilized cells were also performed on this inverted microscope system.

Morphology of pure Gtn-HPA hydrogel fibers was also characterized with a field emission SEM (JEOL JSM-7400F) at an acceleration voltage of 8.0 kV and a working distance of 8.0 mm. Before the fibers were loaded into the SEM chamber for imaging, samples of pure hydrogel fibers were first rinsed in sufficient deionized (DI) water to remove the residues of PBS, followed by freezing in a 35-mm petri dish at −80° C. for 12 h. Next, the frozen samples were dehydrated in a freeze dryer (Labconco Freezone 12L) for 24 h. To reveal the porous structures within the hydrogel fibers, the dried samples were broken into short segments in liquid nitrogen. The segments were then fixed on a stage using a conductive tape, and sputter-coated with platinum for 80 sec.

The distribution of cells in the hydrogel fibers were checked by cryosectioning and DAPI staining. Hydrogel fibers were cut into short segments, and fixed with tissue embedding medium Tissue-Tek™ (Sakura Finetek, Japan) at −80° C. for 12 h. The frozen fiber segments were then sectioned by a cryostat (LEICA CM3050S) to a thickness of 10 µm each, and transferred to microscopy glass slides for DAPI staining. The sectioned samples on microscopy glass slides were washed once with 1×PBS solution, and the cells were fixed with 70% ethanol for 20 min at room temperature. After applying PBS-buffered DAPI solution (10 µg/ml), the samples were left at room temperature for about 15 min, and washed with 1×PBS solution. The cell morphology was observed using the inverted fluorescence microscope (Olympus IX71) at an excitation wavelength of 350 nm.

Other features, benefits and advantages of the present invention not expressly mentioned above can be understood from this description and the drawings by those skilled in the art.

Although only exemplary embodiments of this invention have been described above, those skilled in the art will readily appreciate that many modifications are possible therein without materially departing from the novel teachings and advantages of this invention.

The invention, rather, is intended to encompass all such modification within its scope, as defined by the claims.

What is claimed is:

1. A process of forming a polymer fiber by hydrodynamic spinning, comprising:
    forcing a plurality of fluids to flow through a conduit and to form a laminar flow comprising three or more layers of generally coaxial fluid flows, said fluid flows flowing at respective flow rates through said conduit selected to define a cross-section of a tubular middle layer of said fluid flows, said middle layer comprising a cross-linkable polymer precursor, another layer of said fluid flows comprising a cross-linking agent;
    wherein substantial diffusion of said polymer precursor away from said middle layer is prevented but a portion of said cross-linking agent is allowed to diffuse from said another layer into said middle layer to facilitate cross-linking of said polymer precursor in said middle layer to form a tubular polymer layer in a polymer fiber, by selecting said polymer precursor, said cross-linking agent, and said fluids and controlling said flow rates, said polymer layer having a cross-section generally corresponding to said cross-section of said middle layer.

2. The process of claim 1, comprising adjusting said flow rates through said conduit to change said cross-section of said tubular middle layer.

3. The process of claim 2, wherein said adjusting comprises adjusting said flow rates during said forcing.

4. The process of claim 2, wherein said adjusting said flow rates comprises adjusting a ratio of said flow rates.

5. The process of claim 1, wherein said another layer comprises a tubular outer layer of said fluid flows.

6. The process of claim 1, wherein said another layer comprises an inner layer of said fluid flows, and said polymer fiber is tubular.

7. The process of claim 6, wherein said polymer fiber has an inner diameter of about 20 µm or larger and an outer diameter of about 60 µm or larger.

8. The process of claim 1, wherein a generally cylindrical inner layer of said fluid flows comprises said polymer precursor, and said polymer fiber is generally cylindrical.

9. The process of claim 8, wherein said polymer fiber has a diameter of about 20 µm or larger.

10. The process of claim 1, wherein said middle layer comprises a plurality of middle layers, and said polymer fiber comprises a plurality of polymer layers.

11. The process of claim 1, wherein said cross-linking agent comprises a cross-linker, and said polymer layer comprises a polymer formed by cross-linking said polymer precursor with said cross-linker.

12. The process of claim 1, wherein said cross-linking agent comprises a cross-linking initiator.

13. The process of claim 1, wherein said cross-linking agent comprises a cross-linking catalyst.

14. The process of claim 1, comprising solidifying said polymer fiber.

15. The process of claim 1, comprising immersing said polymer fiber in a liquid bath after said polymer fiber has exited said conduit.

16. The process of claim 1, comprising dispersing a cell in said laminar flow so that said polymer fiber comprises said cell.

17. The process of claim 1, comprising dispersing cells in a plurality of said layers of said laminar flow so that a plurality of layers in said polymer fiber comprise cells.

18. The process of claim 17, wherein said cells are dispersed in said laminar flow such that different layers of said polymer fiber comprise different types of cells.

19. The process of claim 17, wherein said cells are dispersed in said laminar flow such that different layers of said polymer fiber comprise different concentrations of cells.

20. The process of claim 1, wherein one or more of said fluids comprises a cell culture medium.

21. The process of claim 1, wherein one or more of said fluids comprises phosphate buffered saline.

22. The process of claim 1, wherein said polymer precursor comprises gelatin-hydroxyphenylpropionic acid, calcium alginate, or polysulfone.

23. The process of claim 1, wherein said cross-linking agent comprises hydrogen peroxide.

24. The process of claim 23, wherein said middle layer of said fluid flows comprises horseradish peroxidase.

25. The process of claim 1, comprising initiating said cross-linking in said middle layer.

* * * * *